US00PP28722P2

(12) United States Plant Patent
Shadow

(10) Patent No.: US PP28,722 P2
(45) Date of Patent: Dec. 5, 2017

(54) ***PRUNUS* TREE NAMED 'GREPEPTWST'**

(50) Latin Name: *Prunus persica*
Varietal Denomination: GREPEPTWST

(71) Applicant: Don Shadow, Winchester, TN (US)

(72) Inventor: Don Shadow, Winchester, TN (US)

(73) Assignee: GREENLEAF NURSERY COMPANY, Park Hill, OK (US)

( * ) Notice: Subject to any disclaimer, the term of this patent is extended or adjusted under 35 U.S.C. 154(b) by 0 days.

(21) Appl. No.: 14/998,936

(22) Filed: Mar. 7, 2016

(51) Int. Cl.
*A01H 5/08* (2006.01)

(52) U.S. Cl.
USPC ..... Plt./194

(58) Field of Classification Search
USPC ..... Plt./194
CPC ..... A01H 5/0868
See application file for complete search history.

(56) References Cited

PUBLICATIONS https://issuu.com/gardendebut/docs/2016_catalog-online; (2016 Garden Debut Catalog, p. 36); Jul. 27, 2015; 0 pages.*

* cited by examiner

*Primary Examiner* — Kent L Bell
(74) *Attorney, Agent, or Firm* — Penny J. Aguirre

(57) ABSTRACT

A new cultivar of *Prunus persica* named 'GREPEPTWST' that is characterized by its contorted branches that result in a contorted, pendulous plant habit, its spring flowers that are double and light pink in color, and its foliage that is contorted (very curly) in aspect.

3 Drawing Sheets

Botanical classification: *Prunus persica.*
Variety denomination: 'Grepeptwst'.

BACKGROUND OF THE INVENTION

The present invention relates to a new and distinct cultivar of *Prunus persica* and will be referred to hereafter by its cultivar name, 'GREPEPTWST'. 'GREPEPTWST' is a new cultivar of peach tree grown as an ornamental landscape plant.

The Inventor discovered the new cultivar as naturally occurring branch mutation of *Prunus persica* 'Peppermint Stick' (not patented) that was growing in a field at his nursery in Winchester, Tenn. in 2010.

Asexual propagation of the new cultivar was first accomplished by budding by the Inventor in Winchester, Tenn. in June of 2010. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GREPEPTWST' as a unique cultivar of *Prunus.*

1. 'GREPEPTWST' exhibits contorted branches that result in a contorted, pendulous plant habit.
2. 'GREPEPTWST' exhibits spring flowers that are double and light pink in color.
3. 'GREPEPTWST' exhibits foliage that is contorted (very curly) in aspect.

'Peppermint Stick', the female parent of 'GREPEPTWST', differs from 'GREPEPTWST' in having an upward and oval growth habit and in having foliage that is flat in aspect. 'GREPEPTWST' can be most closely compared to the *Prunus persica* varieties 'Bonfire' (not patented) and 'Corinthian Rose' (U.S. Plant Pat. No. 11,564). 'Bonfire' differs from 'GREPEPTWST' in being shorter in height and narrower in width, in having branches that are straight (not contorted), in having foliage that is red in color and in having flowers that are pink to red in color. 'Corinthian Rose' is similar to 'GREPEPTWST' in having double flowers in spring. 'Corinthian Rose' differs from 'GREPEPTWST' in having a columnar plant habit, in having foliage that is flat in aspect, and in having flowers that are darker pink in color.

BRIEF DESCRIPTION OF THE DRAWINGS

The accompanying colored photographs illustrate the overall appearance and distinct characteristics of the new cultivar, 'GREPEPTWST'. The photographs were taken of a four year-old plant of 'GREPEPTWST' as grown outdoors in a trial bed in Winchester, Tenn.

The photograph in FIG. 1 provides a side view of a plant of 'GREPEPTWST'.

Figure 1:
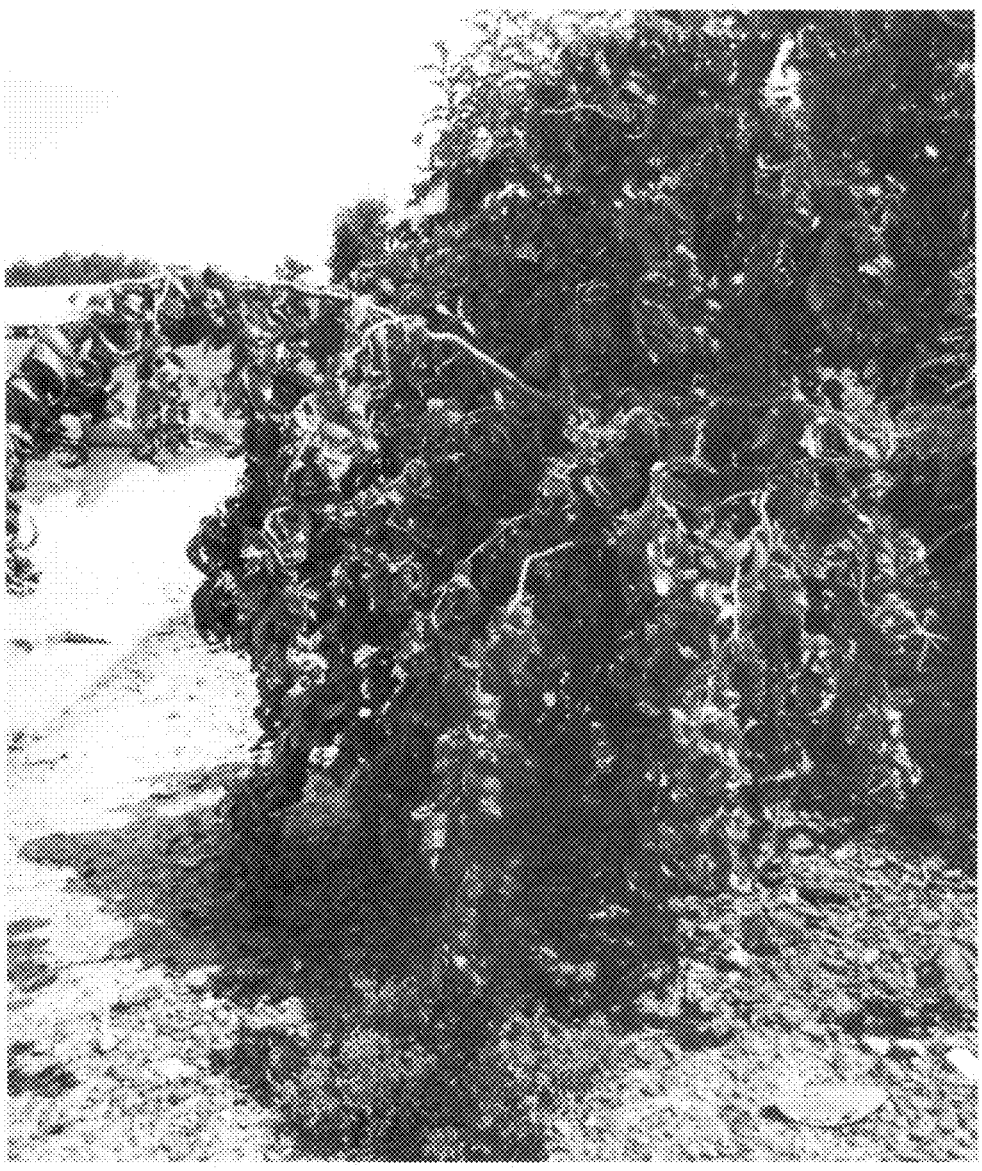
Figure 2:
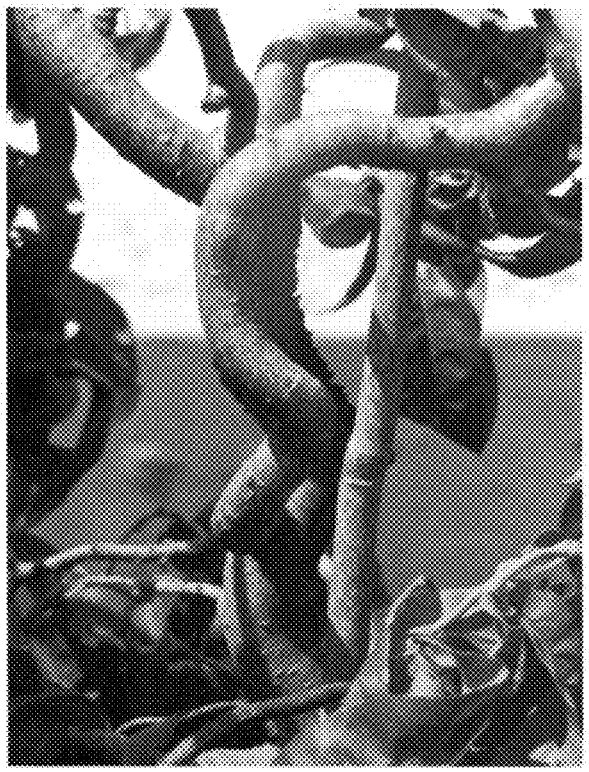

The photograph in FIG. 2 provides a close-up view of the contorted branches of 'GREPEPTWST'.

Figure 3:
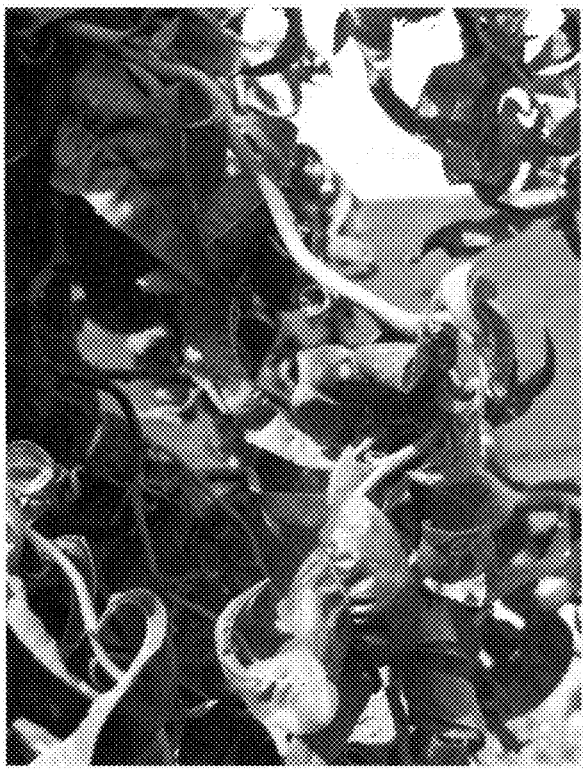

The photograph in FIG. 3 provides a close-up view of the foliage of 'GREPEPTWST'.

Figure 4:
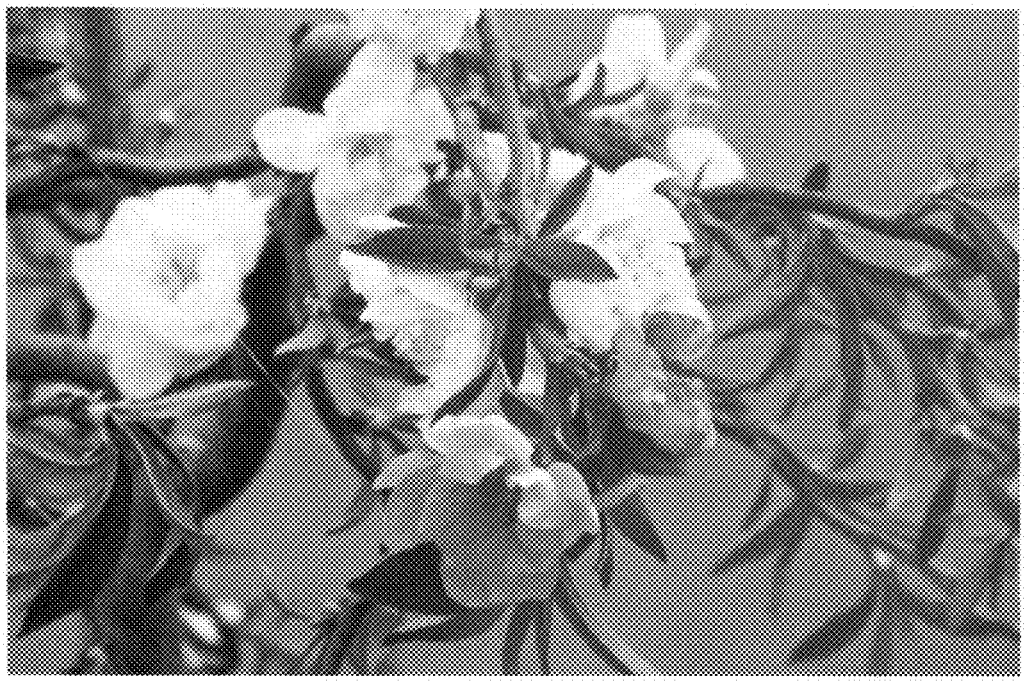

The photograph in FIG. 4 provides a close-up view of the flowers of 'GREPEPTWST'.

Figure 5:
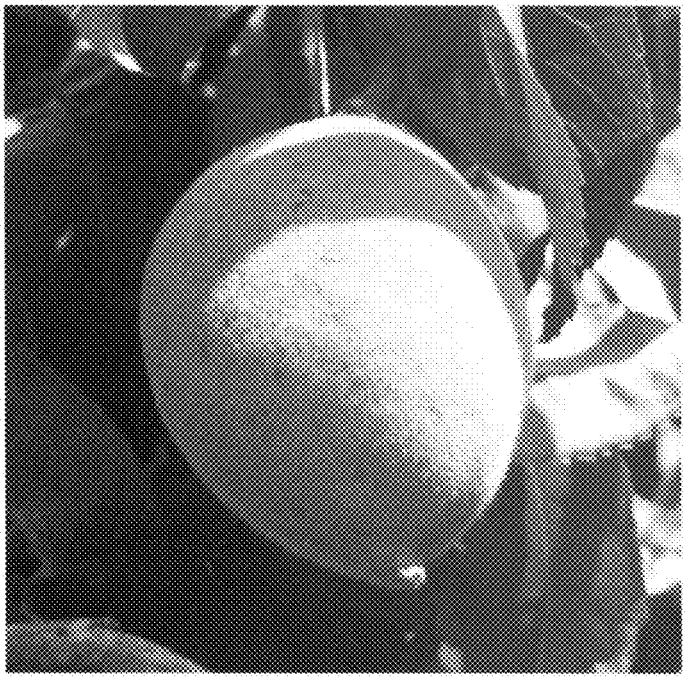

The photograph in FIG. 5 provides a close-up view of a fruit of 'GREPEPTWST'.

The colors in the photographs are as close as possible with the digital photography and printing techniques utilized and the color codes in the detailed botanical description accurately describe the new *Prunus.*

DETAILED BOTANICAL DESCRIPTION

The following is a detailed description of three year-old trees as grown outdoors in 2-gallon containers in Park Hill, Okla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Deciduous tree.

*Plant habit.*—Contorted and pendulous.

*Blooming period.*—3 weeks in spring in Winchester, Tenn.

*Height and spread.*—Reaches an average of 4.6 m in height and about 3 m in width.

*Cold hardiness.*—At least to U.S.D.A. Zones 5 to 8.

*Diseases and pests.*—No susceptibility or resistance to diseases or pests has been observed.

*Root description.*—Fibrous, freely branched.

*Propagation.*—Budding.

*Growth rate.*—Moderate.

Trunk description (main stem):

*Stem size.*—90 cm in length and 1.5 cm in diameter measured 10 cm above soil level.

*Bark color.*—A blend of 199A and 197A with fine fissure lines of 164D.

*Bark texture.*—Relatively smooth barked with fine fissures.

*Lenticels.*—Horizontal, oblong about 2 mm in length and 1 mm in width, 164D in color, about 7 per stem that is 2 cm in length.

*Stem aspect.*—Contorted (twisted), in general changing the direction at each node.

Lateral branches:

*Branch pubescence.*—Absent.

*Branch size.*—An average of 38 cm in length and 4 mm in diameter.

*Anthocyanin presence.*—Absent.

*Branch color.*—144A with minute spots of 144D.

*Branch surface.*—Smooth with sparse lenticels.

*Branch angle.*—Cascading downward from node.

*Branch aspect.*—Contorted (twisted).

*Lenticels.*—Sparse in most regions, 0 to 3 per stem that is 2 cm length, 2 mm in length and 1.5 mm in width, 165A in color.

*Branch internode length.*—An average of 2.7 cm.

*Vegetative buds.*—An average of 4 mm in length and width, conical in shape, 165A in color, comprises 3 ovate sections of pubescent imbricate scales.

Foliage description:

*Leaf shape.*—Lanceolate.

*Leaf division.*—Simple.

*Leaf base.*—Cuneate.

*Leaf apex.*—Acuminate.

*Leaf fragrance.*—None.

*Leaf burst.*—Typically 1$^{st}$ week of May.

*Leaf venation.*—Pinnate, only prominent on lower surface, upper surface 144A, lower surface mid rib is 139D with other veins matching leaf color.

*Leaf margins.*—Finely serrated.

*Leaf arrangement.*—Alternate with secondary leaves emerging from the same node in a whorl (typically two — that develop like the primary leaf).

*Leaf aspect.*—Concave, puckered, and contorted (very curly) both longitudinally and laterally.

*Leaf attachment.*—Petiolate.

*Leaf surface.*—Glabrous and dull on upper and lower surface.

*Leaf size.*—Mature leaves up to 10 cm in length and 3 cm in width.

*Leaf internodes.*—An average of 2.2 cm.

*Leaf color.*—Newly expanded leaves (folded inward at midrib) upper and lower surface; 144A, mature leaves upper surface; N137B, mature leaves lower surface; 147B.

*Petioles.*—Sulcate on lower surface, average of 1 cm in length and 1.5 mm in width, color 144A on upper surface and 137B on lower surface, glabrous surface texture.

Inflorescence description:

*Inflorescence type.*—1 to 2 double flowers on axillary nodes.

*Lastingness of inflorescence.*—Individual flowers last about 7 days.

*Inflorescence size.*—Up to 3 cm in width and 1.5 cm in depth when 2-flowered.

*Flower fragrance.*—None detected.

*Flower quantity.*—Average of 20 per stem 25 cm in length.

*Flower type.*—Rotate, fully double, only partially open.

*Flower size.*—Up to 1.7 cm in diameter and depth.

*Flower buds.*—An average of 1.2 cm in height and 1 cm in diameter, color; apex N155A or 62C or 63C, base 138A, surface; apex glabrous, base pubescent.

*Calyx.*—Comprised of 5 un-fused and spreading sepals.

*Epicalyx.*—5 segments, fused into conical base, base is 3 mm in length and 4 mm in width, lobes are elliptic-ovate in shape, apex acute, entire margins, an average of 5 mm in length and 3 mm in width, inner and outer surfaces pubescent, color of all surfaces 138A in color.

*Sepals.*—5, un-fused, overlapping with epicalyx lobes, elliptic in shape, entire margins, acute apex, cuneate base, pubescent on both surfaces, average of 4 mm in length and 3 mm in width.

*Petals.*—An average of 24 (with very center ones petiole-like), oval to broadly oval in shape (center petiole-like ones irregular), un-fused, overlapping, entire margin, cuneate base, broadly acute apex, cupped in aspect, up to 1.1 cm in length and width, upper and lower surface color (varies between 3 different colorations; N155A (with occasional marking of 62C) or 62C to 62D or 63B to 63C with occasional markings of N155A or 62C, glabrous on upper and lower surface.

*Peduncles.*—Average of 3 mm in length, 2 mm in width, 138A in color, glabrous surface texture, moderately strong.

*Pedicels.*—None.

Reproductive organs:

*Gynoecium.*—Pistil; 1, style; 145C in color, an average of 1 cm in length, highly pubescent surface, stigma; an average of 1.5 mm in diameter and 137B in color, ovary is superior, glossy and slightly pubescent surface, conical in shape and 144D in color.

*Androecium.*—Stamens; average of base adnate to calyx, filaments; 155A in color, an average of 1 cm in length and 0.5 mm in width, pubescent surface, anthers; 162C in color, dorsifixed, an average of 1.5 mm in length and 1 mm in width, pollen is moderate in quantity and 13B in color.

Fruit description:

*Fruit type.*—Drupe.

*Fruit shape.*—Kidney-shaped (lateral view is flattened), flat apex.

*Fruit apex.*—Flat with low susceptibility to rain induced cracking.

*Fruit size.*—4.5 cm in length and 4 cm in width.

*Fruit firmness.*—Firm.

*Fruit set.*—Low.

*Fruit stalk.*—An average of 6 mm in length and 4 mm in width, surface color N141D.

*Fruit bearing.*—Low.

*Number of fruit.*—Average of 1 per axillary node.

*Skin color.*—N141D.

*Produced.*—August in Winchester, Tenn.

*Skin surface.*—Matt and pubescent.

*Flesh color.*—145C.

*Flesh texture.*—Firm.

*Flavor.*—Insipid, non-edible.

*Weight.*—An average of 75 g/berry.

*Seeds.*—1 stone per berry, 165A in color, an average of 2.3 cm in length and 1.6 cm in width, semi adherent to flesh, shape; lateral view is flattened oval, front view oval with acute base, keel is very strongly developed.

It is claimed:

1. A new and distinct cultivar of *Prunus* tree named 'GREPEPTWST' as herein illustrated and described.

* * * * *